(12) United States Patent
Gogolewski

(10) Patent No.: US 9,511,173 B2
(45) Date of Patent: *Dec. 6, 2016

(54) BIOCOMPATIBLE, BIODEGRADABLE POLYURETHANE MATERIALS WITH CONTROLLED HYDROPHOBIC TO HYDROPHILIC RATIO

(71) Applicant: DEPUY SYNTHES PRODUCTS, INC., Raynham, MA (US)

(72) Inventor: Sylwester Gogolewski, Davos Platz (CH)

(73) Assignee: DePuy Synthes Products, Inc., Raynham, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 14/706,576

(22) Filed: May 7, 2015

(65) Prior Publication Data

US 2015/0231305 A1 Aug. 20, 2015

Related U.S. Application Data

(63) Continuation of application No. 13/914,549, filed on Jun. 10, 2013, now Pat. No. 9,061,089, which is a continuation of application No. 11/572,648, filed as application No. PCT/CH2004/000471 on Jul. 26, 2004, now Pat. No. 8,460,378.

(51) Int. Cl.
| | |
|---|---|
| *A61L 31/06* | (2006.01) |
| *C08G 18/22* | (2006.01) |
| *C08G 18/32* | (2006.01) |
| *C08G 18/38* | (2006.01) |
| *A61L 27/58* | (2006.01) |
| *C08G 18/68* | (2006.01) |
| *C08G 18/73* | (2006.01) |
| *A61L 27/18* | (2006.01) |
| *A61L 27/54* | (2006.01) |
| *A61L 27/56* | (2006.01) |

(52) U.S. Cl.
CPC ............... *A61L 27/58* (2013.01); *A61L 27/18* (2013.01); *A61L 27/54* (2013.01); *A61L 27/56* (2013.01); *C08G 18/3203* (2013.01); *C08G 18/68* (2013.01); *C08G 18/73* (2013.01)

(58) Field of Classification Search
CPC ... C08L 75/04; C08G 18/222; C08G 18/3271; C08G 18/3819; C08G 18/4018; C08G 18/4277; C08G 18/4833; C08G 18/664; C08G 2230/00; Y10T 428/249953
See application file for complete search history.

(56) References Cited

U.S. PATENT DOCUMENTS

| | | | |
|---|---|---|---|
| 5,496,909 A | 3/1996 | Muhlfeld et al. | |
| 5,674,921 A * | 10/1997 | Regula et al. | 522/97 |
| 5,756,632 A * | 5/1998 | Ward et al. | 528/28 |
| 5,898,049 A | 4/1999 | Muller et al. | |
| 6,383,190 B1 | 5/2002 | Preissman | |
| 8,460,378 B2 | 6/2013 | Gogolewski | |
| 9,061,089 B2 | 6/2015 | Gogolewski et al. | |
| 2004/0151930 A1 | 8/2004 | Rouns et al. | |

FOREIGN PATENT DOCUMENTS

| | | | | |
|---|---|---|---|---|
| JP | 03-85179 | 4/1991 | | |
| JP | 04-221538 | 8/1992 | | |
| JP | 07-313586 | 12/1995 | | |
| JP | 08-024347 | 1/1996 | | |
| JP | 09-201330 | 8/1997 | | |
| WO | WO 91/19470 | * 12/1991 | ............ | A61F 13/00 |
| WO | WO 01/32100 A2 | 5/2001 | | |
| WO | WO 02/10244 | 2/2002 | | |
| WO | WO 2004/069890 | 8/2004 | | |
| WO | WO 2006/010278 | 2/2006 | | |

OTHER PUBLICATIONS

Gorna et al. (Journal of Biomedical Materials Research, vol. 60, Issue 4, pp. 592-606, Jun. 2002).*
Gorna (Synthetic Bioabsorbable Polymers for Implants, 2000, 39-56) hereinafter known as Gorna-.*
Gorna et al., "In Vitro Degradation of Novel Medial Biodegradable Polyurethanes Based on Epsilon-Caprolactone and Pluronics with Various Hydrophlicitites", Polymer Degradation and Stability 75, 2002, pp. 113-122.
Pavlova et al., "Biocompatible and Biodegradable Polymers", Biomaterials 1993, vol. 14, No. 13, pp. 1024-1029.
European Patent Application No. 04750971.6, Communication Mailed Jun. 12, 2008, 5 pages.
International Application Serial No. PCT/CH2004/000471, International Preliminary Report on Patentability dated Oct. 30, 2006, 12 pages.
International Application Serial No. PCT/CH2004/000471, Written Opinion Mailed Mar. 14, 2005, 5 pages.
Japanese Application No. 2002-506661, Notice of the Reason for the Rejection mailed Feb. 27, 2008, (w/English Translation), 7 pages.
Japanese Application No. 2002-506661, Official Notice of Reason for the Final Rejection mailed Jul. 11, 2008, (w/English Translation), 4 pages.

(Continued)

*Primary Examiner* — Anna Falkowitz
(74) *Attorney, Agent, or Firm* — Baker & Hostetler LLP

(57) ABSTRACT

The biocompatible, biodegradable materials in the solid and/or liquid form are based on segmented linear polyurethanes and/or segmented crosslinked polyurethanes based on A) one or more biocompatible polyols susceptible to hydrolytic and/or enzymatic degradation having a molecular weight of 100 to 20,000 dalton and a number of active hydroxyl groups per molecule (functionality) of at least two or higher: B) one or more diisocyanates and/or triisocyanates; and C) one or more low molecular weight chain extenders having a molecular weight of 18 to 1000 dalton and the functionality of at least two or higher.

34 Claims, No Drawings

(56) References Cited

OTHER PUBLICATIONS

Kaneko et al., "Synthesis and Swelling—Deswelling Kinetics of Poly(N-isopropylacrylamide) Hydrogels and Grafted with LCST Modulated Polymers", Journal of Biomaterials Science, Polymer Edition 10(11), 1999, 1079-1091.
Stile et al., "Synthesis and Characterization of Injectable Poly(N-isopropylacrylamide)-Based Hydrogels That Support Tissue Formation in Vitro", Macromolecules, 32, 1999, 7370-7379.
Fromstein et al., "Elastomeric Biodegradable Polyurethane Blends for Soft Tissue Applications", J. Biomaterial Science Polym., Edition, 2002, 13(4), 391-406.
Ruiz et al., "Phosphorylcholine-Containing Polyurethanes for the Control of Protein Adsorption and Cell Attachment via Photoimmobilized Laminin Oligopeptides", J. Biomaterials Science Polym., Edition, 1999, 10(9), 931-955.
Gorna et al., "Preparation, Degradation and Calcification of Biodegradable Polyurethane Foams for Bone Graft Substitutes", J. Biomed Mater Res A., Dec. 1, 2003, 67(3), 813-827.
European Search Report for European Patent Application No. 04738111.6 dated Apr. 30, 2013, 4 pages.

\* cited by examiner

BIOCOMPATIBLE, BIODEGRADABLE POLYURETHANE MATERIALS WITH CONTROLLED HYDROPHOBIC TO HYDROPHILIC RATIO

This application is a continuation of U.S. application Ser. No. 13/914,549, filed Jun. 10, 2013 (now allowed), which is a continuation of U.S. application Ser. No. 11/572,648, filed Apr. 7, 2008, now U.S. Pat. No. 8,460,378, which is a National Stage Entry of International Application No. PCT/CH04/00471, filed Jul. 26, 2004, published as WO2006/010278 on Feb. 2, 2006, each of which are incorporated herein by reference in their entirety.

The invention relates to biocompatible, biodegradable materials according to the preamble of claim 1.

The advantages achieved by the invention are essentially to be seen in the fact that the polyurethane according to the invention can be produced with a controlled elasticity, i.e. can be either stiff or elastic depending on the intended application of the material. The polyurethane materials according to the invention can also be made injectable which enhances their implantation using syringes or other suitable devices for cement delivery. The chemical structure of the polyurethane materials according to the invention can be designed as to enhance interaction with cells and tissues and ensure controlled degradation. The material can readily be transformed into porous scaffolds for tissue repair and engineering using available production techniques.

Linear and/or crosslinked biodegradable, segmented polyurethanes containing labile and/or biologically active moieties and polyurethaneacrylates are produced from biocompatible polyols or the mixtures of polyols having various hydrophilicity, aliphatic diisocyanates, various chain extenders, having preferably but not exclusively biological activity and biocompatible acrylates containing at least one hydroxyl group. The use of aliphatic diisocyanates avoids problems with carcinogenic diamines which are formed upon degradation of polyurethanes based on aromatic diisocyanates, e.g. 4,4'-diphenylmethane diisocyanate. The use of mixtures of polyols with various hydrophilicities allows producing materials with controlled hydrophilic-to-hydrophobic content ratio and degradation rates, the use of chain extenders or polyols having biological activity, enhances positive interaction of implantable devices from the polyurethanes of the invention with cells and tissues and may promote tissue healing and regeneration, and the use of hydroxyacrylates in combination with mentioned above reagents allows for the preparation of injectable materials with adjustable rigidity, e.g. for the treatment of osteoporotic vertebrae, spine disc diseases or large bone defects. The polyurethanes of the invention may contain various additives of organic and inorganic origin to additionally enhance their mechanical and biological properties.

The biologically active moieties can be chemically incorporated in the polymer back bone constituting a part of its structure, can be attached to the backbone as pending fragments, e.g. forming a branched system, or can be physically attached to the materials using the physical interactions such as ionic interaction, adhesion, capillarity effect or diffusion.

This invention relates to biocompatible, biodegradable polyurethane and polyurethaneacrylate materials with controlled elastic properties, hydrophilicity, degradation rates and porosity, to be used in implantable medical devices or as topical wound covers.

Depending on the chemical composition, elastic properties, hydrophilicity, degradation rates and porosity, the polyurethanes and polyurethaneacrylates of the invention can be used as adhesion barriers, scaffolds for the repair and regeneration of various tissues, solid tissue defect fillers and liquid injectable materials which solidify after injection.

Polyurethanes are a weft-known class of materials with the characteristic —NH—CO—O—linkage in the chain. The polymers are obtained in the reaction of diisocyanates with oligomeric diols also called polyols to produce a macrodilsocyanate or a prepolymer, and the synthesis is completed by re-acting macrodiisocyanates with low molecular weight two-functional or more-functional chain extenders:

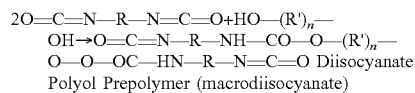
2O=C=N—R—N=C=O+HO—(R')$_n$—
OH→O=C=N—R—NH—CO—O—(R')$_n$—
O—O—OC—HN—R—N=C=O Diisocyanate Polyol Prepolymer (macrodiisocyanate)

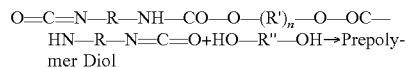
O=C=N—R—NH—CO—O—(R')$_n$—O—OC—
HN—R—N=C=O+HO—R"—OH→Prepolymer Diol

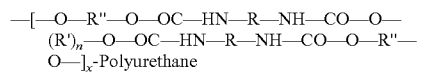
—[—O—R"—O—OC—HN—R—NH—CO—O—
(R')$_n$—O—OC—HN—R—NH—CO—O—R"—
O—]$_x$-Polyurethane

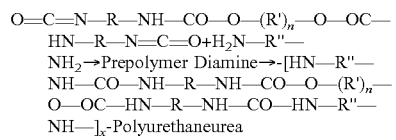
O=C=N—R—NH—CO—O—(R')$_n$—O—OC—
HN—R—N=C=O+H$_2$N—R"—
NH$_2$→Prepolymer Diamine→-[HN—R"—
NH—CO—NH—R—NH—CO—O—(R')$_n$—
O—OC—HN—R—NH—CO—HN—R"—
NH—]$_x$-Polyurethaneurea Polyols used in the synthesis have molecular weights in the range of 100 to 20,000 dalton (preferably 200 to 10,000 dalton) and are primarily based on polyesters or polyethers, although diols of other oligomeric compounds are also used to produce polyurethanes. The chain extenders are low molecular weight diols, diamines, triols, triamines or higher molecular weight oligomeric units having the functionality of two or higher. The use of two-functional chain extenders leads to thermoplastic, linear block copolymers of the (AB) type, while the use of three-functional chain extenders such as triols, friar mines or water leads to crosslinked materials. The structure of segmented polyurethanes consists of the relatively flexible soft segment derived from polyols, and the hard segments containing diisocyanate and chain extender species. Preferably the hard segment content is in the range of 5 to 100% and the soft segment forms the remaining part of the polyurethane material.

High-purity medical segmented polyurethanes with a wide range of physical and chemical properties are used in various extracorporeal and implantable devices. One of the problems with implantable polyurethanes is their relatively poor molecular stability in the aggressive environment of the body tissues. Degradation of polyurethanes in vivo proceeds mainly through hydrolytic chain scission within ester and urethane linkages and oxidative attack within polyether segments. This appears to be accelerated by the action of cell enzymes, peroxides, the catalytic activity of metal ions, the formation of carboxylic groups, lipids pickup, calcification, the stress or load acting on the implants, phagocytosis and lysis of material fragments by macrophages and giant cells.

Susceptibility of polyurethanes to in vivo degradation can deliberately be exploited to design biodegradable polyurethane materials. Biodegradable polyurethanes can be synthesized by incorporating in the polymer chain labile moieties, susceptible to hydrolysis and/or to specific enzymes.

Depending on the mechanical properties, chemical composition and surface characteristics of biodegradable polyurethanes they can potentially be used for cardiovascular implants, drug delivery devices, nonadhesive harriers in trauma surgery, bone graft substitutes, injectable augmentation materials, tissue—organ regeneration scaffolds (tissue engineering), or adhesives.

The type of monomers used in the syntheses of biodegradable polyurethanes will to a great extent be dependent on the intended application of the material. Hydrophilic polyurethane elastomers are preferred for the preparation of implants to be used in contact with blood or as adhesion barriers, although the ratio between the hydrophilic and hydrophobic components in polyurethanes seems to play an important role in the contact of the material surface with blood proteins and cells. The polyurethanes based on polyethylene oxide are highly hydrophilic materials. At higher polyethylene oxide content, these polymers in the aqueous environment behave like hydrogels, taking up to 200% of water depending on their chemical composition. They are nonadhesive to proteins, cells and tissues. Thus, polyurethanes with higher amounts of hydrophobic component may be required for bone graft substitutes and for cell culture. It should be kept in mind, however, that hydrophobicity is only one of many characteristics, which determine the interaction of polyurethanes with cells and tissues.

Polyurethaneacrylates can be produced from urethane prepolymers by reacting them with acrylates containing at least one hydroxyl group. The reaction yields a prepolymer terminated with acrylic linkage:

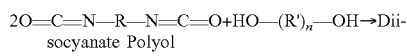
2O=C=N—R—N=C=O+HO—(R')$_n$—OH→Diisocyanate Polyol

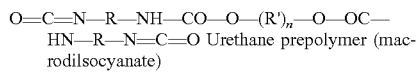
O=C=N—R—NH—CO—O—(R')$_n$—O—OC—HN—R—N=C=O Urethane prepolymer (macrodiisocyanate)

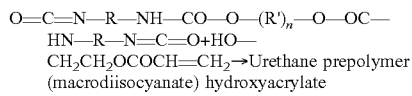
O=C=N—R—NH—CO—O—(R')$_n$—O—OC—HN—R—N=C=O+HO—CH$_2$CH$_2$OCOCH=CH$_2$→Urethane prepolymer (macrodiisocyanate) hydroxyacrylate

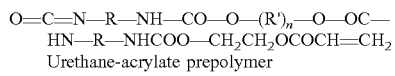
O=C=N—R—NH—CO—O—(R')$_n$—O—OC—HN—R—NHCOO—CH$_2$CH$_2$OCOCH=CH$_2$
Urethane-acrylate prepolymer This can be subsequently polymerized by chemically-induced or radiation-induced free-radical polymerization.

Commodity commercial acrylic urethanes are used as one and two-component coatings for weatherable applications. Biodegradable acrylic urethanes of this invention based on biocompatible labile polyols can find applications as injectable bone substitutes and tissue void fillers.

There were various biodegradable polyurethanes described in the published literature. The labile moieties used in the synthesis of these polyurethanes were for example polyols from lactic acid and ethylene diol and/or diethylene diol, lactic acid and 1,4-butanediol, butyric acid and ethylene diol, monomers containing peptide links, sugar derivatives, hydroxy-terminated copolymers of L-lactide-ε-caprolactone, glycolide-ε-caprolactone, ε-caprolactone-co-δ-valerolactone, lysine diisocyanate or L-lysine, polyethylene oxide), poly(ε-caprolactone) and amino acid-based chain extender.

The polyurethane materials according to the invention may be linear and/or crosslinked biodegradable, segmented polyurethanes and polyurethaneacrylates containing labile and/or biologically active moieties. These material may be used as implantable medical devices containing such polyurethanes. The biodegradable polyurethanes of the invention are based on biocompatible polyols or the mixtures of polyols having various hydrophilicity allowing producing materials with controlled hydrophilic-to-hydrophobic content ratio, preferably although not exclusively aliphatic diisocyanates or triisocyanates, various chain extenders, having preferably but not exclusively biological activity, and/or biocompatible hydroxyacrylates.

The polyurethane-acrylate material is preferably chosen from: cyclohexane dimethanol dimethacrylate, cyclohexane dimethanol diacrylate, alkoxylated hexanediol diacrylate, alkoxylated cyclohexane dimethanol diacrylate, caprolactone modified neopentylglycol hydroxypivalate diacrylate, ethylene glycol dimethacrylate, tetraethylene glycol dimethacrylate, polyethylene glycol dimethacrylate, 1,4-butanediol diacrylate, 1,4-butanediol dimethacrylate, diethylene glycol diacrylate, diethylene glycol dimethacrylate, 1,6-hexanediol diacrylate, 1,6-hexanediol dimethacrylate, neopentyl glycol diacrylate, neopentyl glycol dimethacrylate, polyethylene glycol diacrylate, tetraethylene glycol diacrylate, dipropylene glycol diacrylate, polyethylene glycol dimethacrylate, polyethylene glycol diacrylate, polyethylene glycol dimethacrylate water solution, propoxylated 2-neopentyl glycol diacrylate, alkoxylated aliphatic diacrylate.

The biocompatible, biodegradable materials may also be based on: aliphatic urethane acrylates, polyester acrylates, polyether acrylates, amine modified polyether acrylates.

The biocompatible, biodegradable materials are typically based on at least to two polyols and preferably at least two of said polyols have a different hydrophilicity.

In one embodiment all of said polyols are hydrophilic, in another embodiment all of said polyols are hydrophobic. However, said polyols may also be a mixture of hydrophilic and hydrophobic polyols. The ratio between hydrophilic monomers and hydrophobic monomers are preferably in the range of 1-4, preferably between 2.0-2.6.

Alternatively at least one polyol may have amphiphilic qualities. The materials become amphiphilic as a result of their architecture, i.e. chemical constitution resulting from the balance between hydrophilic and hydrophobic segments or groups in the polymeric chain upon synthesis.

The biocompatible polyols which are used separately or as mixtures in the synthesis of the polyurethanes and polyurethaneacrylates of the invention have molecular weights in the range of 100 to 20,000 dalton, preferably 400 to 12,000 dalton, and most preferably 400 to 6000 dalton. The polyols are based on polyesters, polyethers, mixtures thereof, and copolymers of esters with ethers.

The polyols suitable for the synthesis of the polyurethanes of the invention are based on hydroxyacids or dicarboxylic acids, the examples of which are lactic acid, citric acid, tartaric acid, adipic acid, succinic acid, sebacic acid, oxalic acid, tannic acid, aspartic acid and azelaic acid. These can be used individually or as a mixture, and diols such as 1,4-butanediol, dipropylene diol, ethylene diol, diethylene diol, 1,5-hexanediol and 1,3-propanediol, neopentyl diol, trimethylene diol, and pentaerythritol, to mention but a few. Other polyols can be polycarbonate diols, poly(ε-caprolactone) diols, poly(ethylene oxide) diols, poly(ethylene oxide-propylene oxide-ethylene oxide) diols known as commercial product under a trade name Pluronics™, polyols based on β-propiolactone, δ-valerolactone and γ-butyrolactone, isosorbide, aminosaccharides and polyols from vegetable oils such and micellar casein as stearic, oleic, linoleic and linolenic for example.

The polyols suitable for the invention have a low molecular stability, which is the inherent ability of the polyol to undergo hydrolytic chain scission in the aqueous environment. When such polyol units are incorporated in polyurethanes, the hydrolytic chain scission proceeds mainly via ester or ether linkages in the polymer chain, depending whether polyether diols or polyester diols were used in the polyurethane synthesis. In polyurethanes water reacts with a carboxylic ester link, which breaks the polymer chain into two shorter ones. One of these ends is a hydroxyl group, while the other end is a carboxyl group. The acidic carboxyl group accelerates the further hydrolysis of the polyester segments and the degradation becomes autocatalytic. The urethane (carbamate) linkage can also be hydrolyzed, but less readily than carboxylic) ester linkages. In polyetherurethanes the ether linkage is relatively resistant to hydrolysis but can be hydrolyzed in the aggressive environment of the living organism. The weakest linkage towards hydrolysis of polyetherurethanes is the urethane linkage. Breakage of the urethane linkage produces two shorter chains terminated with hydroxyl and amino groups.

The diisocyanates and polydiisocyanates suitable for the synthesis of the polyurethanes of the invention are aliphatic or aromatic diisocyanates, triisocyanates or polyisocyanates. They can be used individually or as mixtures in various proportions. Examples of aliphatic diisocyanates are 1,6-hexamethylene diisocyanate, 1,4-diisocyanato butane, L-lysine diisocyanate, isophorone diisocyanate, 1,4-diisocyanato 2-methyl butane, 2,3-diisocyanato 2,3-dimethyl butane, 1,4-di(1propoxy-3-diisocyanate, 1,4-diisocyanato 2-butene, 1,10-diisocyanato decane, ethylene diisocyanate, 2,5 bis(2-isocyanato ethyl) furan, 1,6-diisocyanato 2,5-diethyl hexane, 1,6-diisocyanato 3-methoxy hexane, 1,5 diisocyanato pentane, 1,12-dodecamethylene diisocyanate, 2 methyl-2,4 diisocyanato pentane, 2,2 dimethyl-1,5 diisocyanato pentane, ethyl phosphonyl diisocyanate, 2,2,4-trimethyl-1,6-hexamethylene diisocyanate. Examples of aromatic diiscocyanates are 4,4'-diphenylmethane diisocyanate, 2,4'-diphenylmethane diisocyanate and 2,2'-diphenylmethane diisocyanate; mixtures of 2,4'-diphenylmethane diisocyanate and 4,4'-diphenylmethane diisocyanate, 2,4-toluene diisocyanate, mixtures of 2,4-toluene diisocyanate and 2,6-toluene diisocyanate, 2,4'-diphenylmethane diisocyanates, 4,4'-diphenylethane diisocyanato and 1,5-naphthylene diisocyanate to mention but a few.

The suitable chain extenders used in the synthesis of polyurethanes of the invention are water, aliphatic difunctional or trifunctional alcohols, amines, aminoalcohols, aminoacids, and hydroxyacids. Examples are 2-aminoethanol, 2-dibutylaminoethanol, n-alkyl-diethanolamines, n-methyl-diethanolamine, ethylene diol, diethylene did, 1,4-butanediol, propylene diol, dipropylene did, 1,6-hexanediol, isosorbide (1,4:3,6-dianhydrosorbitol), glycerol, ethylene diamine, tetramethylene diamine, hexamethylene diamine, isophorone diamine, propanolamine, ethanolamine, glycyl-L-glutamine, glycyl-L-tyrosine, L-glutathione, glycyl glycine, L-malic acid and mixtures of these compounds.

The examples of suitable physiologically active chain extenders are oligosaccharides (chitosan-oligosaccharides with the D-glucosamines bonded by β-1,4 bonding, maltooligosaccharides, chitoollgosaccharides), sugar alcohols, cyclodextrins creatine, modified soy, various aminoalcohols (L-alaninol, L-asparginol, L-glutaminol, L-glycinol, L-lysinol, L-prolinol, L-tryptophanol, pyrrolidinemethanol, isoleucinol), various aminoacids, glycyl-L-glutamine, glycyl-L-tyrosine, L-glutathione, glycylglycine, L-malic acid.

The functionality of the chain extenders may relate to the following functional groups: —OH, —NH$_2$, —SH, or —COOH.

The chain extenders have preferably a molecular weight in the range 18 to 500. Preferably they have biologically and/or pharmacologically active properties.

In a further embodiment a biologically and/or pharmacologically active component is incorporated chemically or physically in the polymer molecule, preferably in an amount of 0.005 to 20% of the total weight of the biocompatible, biodegradable material.

Said biologically and/or pharmacologically active components may be chosen from: creatine, oligosaccharides (chitosan-oligosaccharides with the D-glucosamines bonded by β-1,4 bonding, maltooligosaccharides, chitooligosaccharides), sugar alcohols, cyclodextrins, modified soy, various aminoalcohols L-asparginol, L-glycinol, L-lysinol, L-prolinol, L-tryptophanol, pyrrolidinemethanol, isoleucinol), various aminoacids, glycyl-L-glutamine, glycyl-L-tyrosine, L-glutathione, glycylglycine, L-malic acid, 2-mercaptoethyl ether, citric acid, ascorbic acid, lecithin, polyaspartates.

Typically the biocompatible, biodegradable materials degrade within 2 to 18 months and preferably within 4 and 12 months.

In a further embodiment the biocompatible, biodegradable materials have a glass transition temperature in the range of −60° C. to +70° C.

Preferably the polyurethane materials—upon degradation—degrade to nontoxic by-products.

The biocompatible, biodegradable materials according to the invention have preferably a molecular weight in the range of 10,000 to 300,000 dalton.

Typically the biocompatible, biodegradable materials have an interconnected porous structure. The pore size is preferably in the range of 0.1 micrometer to 5000 micrometers.

The biocompatible materials according to the invention may be used for the manufacture of implantable medical devices, in particular for micro- and/or macroporous membranous and/or spongy structures or bodies which bay be designed as:
  a scaffold suitable for bone substitute, articular cartilage repair or soft tissue repair;
  an artificial periosteum.
  artificial skin or as a wound dressing.
  a cardiovascular implant, preferably as pericardial patch or as a vascular prostheses.
  a bone graft substitute.
  an articular cartilage repair.
  a tissue engineered scaffold.

The micro- and/or macroporous membranous and/or spongy structures may contain micrometer size or nanosize calcium phosphate crystals. Their complete degradation is preferably in the range of 1 month to 24 months.

The biocompatible materials according to the invention may also be used for the manufacture of nonporous structures for the delivery of various drugs. Such nonporous structures may contain a deliverable growth factor or a deliverable antibiotic or a antibacterial drug. They may be designed as a tissue adhesion barrier or in such a form to be suitable for delivery of injectable polymeric and ceramic cements.

The materials according to the invention may be also designed as a surgical suture or as a an internal fixation device for bone fracture treatment.

Further objects, features and advantages of the invention will be described in more detail with reference to the following examples.

The catalysts used in the synthesis are stannous octoate and dibutyltin dilaurate, but preferably ferric acetylacetonate, magnesium methoxide, zinc octoate and manganese 2-ethylhexanoate. Examples of acrylic monomers used in the synthesis of polyurethaneacrylates of the invention are hydroxyfunctional acrylates, such as 2-hydroxyethyl acrylate, alkoxylated hexanediol diacrylate, caprolactone-modified neopentyldiol, hydroxypivalate diacrylate, 2-hydroxyethyl acrylate, hydroxypropyl acrylate, 2-hydroxyethyl methacrylate, methacrylate and glycerolmonomethacrylate.

EXAMPLE I

Linear polyurethanes were synthesized in bulk at 60° C. in a two-step process. The reagents used were aliphatic hexamethylene diisocyanate, isophorone diisocyanate, poly(ε-caprolactone) diols with molecular weights of 530, 1250 and 2000, 1,4-butane diol, 2-amino-1-butanol, thiodiethylene diol, and 2-mercaptoethyl ether chain extenders, and the catalysts were stannous octoate, dibutyltin dilaurate, ferric acetylacetonate, magnesium methoxide, zinc octoate and manganese 2-ethylhexanoate. The diisocyanate to polyol and chain extender ratio was 2:1:1. The polyurethane polymers obtained had the average molecular weights in the range of 70,000 to 280,000 dalton, the glass transition temperatures in the range of –38° C. to –57° C., the tensile strengths in the range of 12 to 63 MPa and the tensile moduli in the range of 8 to 107 MPa.

EXAMPLE II

Linear segmented polyester-ether urethanes with hydrophilic-to-hydrophobic ratios of 30:70, 40:60, 50:50 and 70:30% were synthesized in bulk at temperatures in the range of 50° C. to 100° C., using polyols with different molecular weights. The hydrophobic component originated from poly(ε-caprolactone) diols with molecular weights 530, 1250, 2000 daltons, the hydrophilic component was based on poly(ethylene oxide) diols with molecular weights of 600 and 2000 daltons or poly(ethylene oxide-propylene oxide-ethylene oxide) diol with molecular weight of 8000 daltons and polyethylene adipate with molecular weight of 1000 daltons. The diisocyanates were hexamethylene diisocyanate and isophorone diisocyanate, the chain extenders were 1,4 butane diol, 3-hexyne-2,5-diol and 2-amino-1-butanol, and the catalyst used were stannous octoate and dibutyltin dilaurate. The polyurethane polymers obtained had viscosity-average molecular weights in the range of 24,000 to 130,000 dalton, tensile strengths at break of 4 to 60 MPa, Young's moduli from 7 to 72 MPa, elongation at break of 100 to 950%, and glass transition temperatures in the range of –116° C. to –41° C.

EXAMPLE III

Crosslinked hydrophobic polyester urethane sponges were synthesized in bulk at temperatures in the range of 50 to 80° C., using poly(ε-caprolactone) diols with molecular weights 530, 1250, 2000 daltons and hexamethylene diisocyanate. The chain extender was an aqueous solution of creatine and the catalyst was manganese 2-ethylhexanoate. The pore-to-volume ratios in the sponges were in the range of 10 to 90%, the compressive strength in the range of 9 to 1960 kPa and the compressive modulus in the range of 15 to 40 MPa.

EXAMPLE IV

Crosslinked polyurethane sponges were synthesized at temperature of 60° C., using polyethylene oxide diols with molecular weight of 600 and 2000 daltons as the hydrophilic component and an aqueous solution of creatine. Ferric acetylacetonate was used as a catalyst. The pore-to-volume ratios in the sponges were in the range of 50 to 70%, the compressive strength in the range of 50 to 2000 kPa, and the compressive modulus in the range of 11 to 35 MPa.

EXAMPLE V

The linear biodegradable aliphatic polyurethanes of varying hydrophilicity as described in example II were subjected to swelling experiments in water. The polymers absorbed water in an amount that increased with the increasing content of the hydrophilic segment in the polymer chain. The total amount of absorbed water did not exceed 2% for the polycaprolactone urethane and was as high as 212% for some poly(caprolactone-ethylene oxide urethanes). Upon in vitro degradation at 37±0.1° C. in phosphate buffer solution the poly(ester urethanes) showed 1 to 2% mass loss at 48 weeks and 1.1 to 3.8% at 76 weeks. The polyester-ether urethanes) manifested 1.6 to 76% mass loss at 48 weeks and 1.6 to 96% at 76 weeks. The increasing content and molecular weight of the polyethylene oxide segment enhanced the rate of mass loss. Similar relations were also observed for polyurethanes from PEO-PPO-PEO (Pluronic) diols. Materials obtained using 2-amino-1-butanol as the chain extender degraded at a slower rate than similar materials synthesized using 1,4-butane diol. All polymers calcified in vitro. The susceptibility to calcification increased with material hydrophilicity.

EXAMPLE VI

The linear polymers described in Examples I-II were processed into three-dimensional porous scaffolds (membranes and sponges) using a phase-inverse process from solutions consisting of a solvent-nonsolvent system and/or solutions containing additives of various salt crystals.

The scaffolds supported the attachment and proliferation of osteoblasts, chondrocytes and myoblasts in culture.

EXAMPLE VII

Crosslinked three-dimensional biodegradable poly ethane scaffolds (foams) with controlled hydrophilicity for bone graft substitutes were synthesized from biocompatible reactants. The scaffolds had hydrophilic-to-hydrophobic content ratios of 70:30, 50:50 and 30:70. The reactants used were hexamethylene diisocyanate or tetramethylene diisocyanate, polyethylene oxide) diol with a molecular weight of 600 dalton (hydrophilic component), and poly(ε-caprolactone) diol with a molecular weight of 2000 dalton, amine-based polyol with a molecular weight of 515 dalton or sucrose-based polyol with a molecular weight of 445 dalton (hydrophobic component). Water alone or aqueous solutions of creatine, aminoalcohols or oligosaccharides were used as the chain extender and foaming agents. Stannous octoate was used as catalysts. Glycerol phosphate calcium salt, calcium carbonate and hydroxyapatite were used as inorganic fillers. The scaffolds had an open-pore structure with pores whose size and geometry depended on the material's chemical composition. The compressive strengths of the scaffolds were in the range of 4 to 340 kPa, the compressive moduli in the range of 9 to 1960 kPa. These values increased with increasing content of polycaprolactone. Of the two materials with the same amount of polycaprolactone the compressive strengths and moduli were higher for the one containing inorganic fillers. The scaffolds absorbed water and underwent controlled degradation in vitro. The amount of absorbed water and susceptibility to degradation increased with the increasing content of the polyethylene oxide segment in the polymer chain and the presence in the material of calcium complexing moiety. All polyurethane scaffolds induced the deposition of calcium phosphate crystals, whose structure and calcium-to-phosphorus atomic ratio depended on the chemical composition of the polyurethane and varied from 1.52 to 2.0.

EXAMPLE VIII

Porous scaffolds from the biodegradable aliphatic polyurethanes with various chemical compositions and the hydrophilic-to-hydrophobic segment ratios as described in Example V were used as cancellous bone graft substitutes in the treatment of monocortical and tricortical bone defects in the ilium of healthy sheep and/or bicortical bone defects in the ilium of estrogen-deficient sheep. Implantation times varied from 6 to 25 months. The ilium defects, which were not implanted with polyurethane scaffolds, were used as controls. In none of the control defects there was bone regeneration at the time of euthanasia. The defects implanted with porous scaffolds from polyurethanes were healed to varying extents with cancellous bone. In the healthy animals the new cancellous bone was radiographically denser than the native bone New bone formed in the scaffolds with the higher amount of the hydrophilic segment contained more hydroxyapatite than bone in the scaffolds with the lower hydrophilic segment content. There was no new cortex formed. In the estrogen-deficient sheep the defects implanted with polyurethane scaffolds were healed with both, the cancellous and cortical bones, although the structure of the new bone was similar to that of native bone. The extents of bone healing were depended on the polymer chemical compositions.

The formation of the new cortex in the ilium defects and the restoration of the full ilium thickness were promoted when the scaffolds implanted in the defect were additionally covered with a microporous biodegradable membrane, which guided the cortex formation and protected against bleeding.

EXAMPLE IX

Porous scaffolds with interconnected pores were produced from biodegradable polyurethanes according to the invention having two different hydrophilic-to-hydrophobic content ratios of 70-30% and 30-70%. The scaffolds with 70% of the hydrophobic component had an average pore size of 100-900 nm and a pore-to-volume ratio of 75%. The scaffolds with 70% of the hydrophilic component had an average pore size of 100-600 nm and a pore-to-volume ratio of 84%. Cylinders 28×42 mm with a central hole along the longitudinal axis were cut from the scaffolds packed and sterilized with a cold-cycle ETO process, followed by evacuation at 50° C. and 3×10-1 mbar for 10 hours. Subsequently the cylinders were impregnated with autogenous bone marrow and implanted in critical-size segmental defects in the sheep tibiae. At 6 months the defects were healed with new bone which grew progressively from the cut bone ends taking over the space occupied initially by the polyurethane scaffold.

Figures 1 to 3 illustrate some of the possible embodiments of the invention, Monocortical, bicortical and tricortical defects in the ilium are implanted with porous scaffolds "a" from biodegradable polyurethanes of the invention and covered with microporous membrane "b". The membrane can be permanently attached to one side of the scaffold or can be placed on bone surface to cover the scaffold and attached to bone with degradable or metallic screws or dowels. Both the membrane and the scaffold can contain various drugs such as growth factors, antibiotics, bacteriostatics, etc.

The invention claimed is:
1. A biocompatible, biodegradable material comprising creatine and segmented linear polyurethane-acrylates and/or segmented crosslinked polyurethane-acrylates, wherein said segmented linear polyurethane-acrylates and/or segmented crosslinked polyurethane-acrylates are prepared from:
   A) at least two biocompatible polyols, wherein said polyols are:
      (i) susceptible to hydrolytic and/or enzymatic degradation and
      (ii) have a molecular weight of 100 to 20,000 daltons and a number of active hydroxyl groups per molecule of at least two or higher;
   B) one or more aliphatic diisocyanates and/or aliphatic triisocyanates;
   C) one or more low molecular weight chain extenders having
      (i) a molecular weight of 18 to 1,000 daltons and
      (ii) the functionality of at least two or higher; and
   D) one or more hydroxyacrylates,
   wherein said biocompatible, biodegradable material is in the form of a micro- and/or macroporous membranous and/or spongy structure or body.

2. The biocompatible, biodegradable material of claim 1, wherein at least two of said polyols have a different hydrophilicity.

3. The biocompatible, biodegradable material of claim 1, wherein all of said polyols are hydrophilic.

4. The biocompatible, biodegradable material of claim 1, wherein all of said polyols are hydrophobic.

5. The biocompatible, biodegradable material of claim 1, wherein at least one of said polyols has amphiphilic qualities.

6. The biocompatible, biodegradable material of claim 1, wherein said polyols are selected from the group consisting of poly(aminobutyrate) diols, poly($\epsilon$-caprolactone) diols, poly(ethylene oxide) diols, amphiphilic poly(ethylene oxide-propylene oxide-ethylene oxide) diols, poly(oxalate diols), aminoalcohols soy diols, cyclodextrins, aminosugars, and sugar alcohols.

7. The biocompatible, biodegradable material of claim 1, wherein said polyols have a molecular weight in the range of 200 to 10,000 daltons.

8. The biocompatible, biodegradable material of claim 1, wherein the functionality of said chain extenders relates to the functional group —OH, —NH2, —SH, or —COOH.

9. The biocompatible, biodegradable material of claim 1, wherein said chain extenders have a molecular weight in the range 18 to 500 daltons.

10. The biocompatible, biodegradable material of claim 1, wherein said chain extenders have biologically and/or pharmacologically active properties.

11. The biocompatible, biodegradable material of claim 1, wherein the creatine is incorporated chemically in the material.

12. The biocompatible, biodegradable material of claim 1, wherein the creatine is incorporated physically in the material.

13. The biocompatible, biodegradable material of claim 1, wherein the creatine is present in an amount of 0.005% to 20% of the total weight of the material.

14. The biocompatible, biodegradable material of claim 1, further comprising one or more biologically and/or pharmacologically active components selected from the group consisting of oligosaccharides (chitosan-oligosaccharides with the D-glucosamines bonded by β-1,4 bonding, maltooligosaccharides, chitooligosaccharides), sugar alcohols, cyclodextrins, modified soy, various aminoalcohols (L-alaninol, L-asparginol, L-glutaminol, L-glycinol, L-lysinol, L-prolinol, L-tryptophanol, pyrrolidinemethanol, isoleucinol), various aminoacids, glycyl-L-glutamine, glycyl-L: tyrosine, L-glutathione, glycylglycine, L-malic acid, 2-mercaptoethyl ether, citric acid, ascorbic acid, lecithin, and polyaspartates.

15. The biocompatible, biodegradable material of claim 1, wherein said aliphatic diisocyanates are selected from the group consisting of 1,6-hexamethylene diisocyanate, 1,4-diisocyanato butane, L-lysine diisocyanate, isophorone diisocyanate, 1,4-diisocyanato 2-methyl butane, 2,3-diisocyanato 2,3-dimethyl butane, 1,4-di(1propoxy-3-diisocyanate, 1,4-diisocyanato 2-butene, 1,10-diisocyanato decane, ethylene diisocyanate, 2,5 bis(2-isocyanato ethyl) furan, 1,6-diisocyanato 2,5-diethyl hexane, 1,6-diisocyanato 3-methoxy hexane, 1,5 diisocyanato pentane, 1,12-dodecamethylene diisocyanate, 2 methyl-2,4 diisocyanato pentane, 2,2 dimethyl-1,5 diisocyanato pentane, ethyl phosphonyl diisocyanate, 2,2,4-trimethyl-1, 6-hexamethylene diisocyanate, 4,4'-dicyclohexylmethane diisocyante ($H_{12}MDI$), trans 1,4-cyclohexane diisocyanate, m-tetramethylxylylen diisocyanate, m-isopropenyldimethylbenzyl, "dimeryl" diisocyanate derived from dimerized linoleic acid, xylylene diisocyanate, and 1,1,6,6-tetrahydroperfluorohexamethylene diisocyanate.

16. The biocompatible, biodegradable material of claim 1, wherein said chain extenders are selected from the group consisting of water, thiodiethylene diol, 2-mercaptoethyl ether, isosorbide diols, citric acid, ascorbic acid, aminobutyric acid, aminoethanol, 2-aminoethanol, 2-dibutylaminoethanol, n-alkyl-diethanolamines, n-methyl-diethanolamine, ethylene diol, diethylene diol, 1,4-butanediol, propylene diol, dipropylene diol, 1,6-hexanediol, 1,4:3,6-dianhydro-D-sorbitol, 1,4:3,6-dianhydro-D-mannitol, 1,4:3, 6-dianhydro-L-iditol, glycerol, ethylene diamine, tetramethylene diamine, hexamethylene diamine, isophorone diamine, pro-panolamine, ethanolamine, glycyl-L-Glutamine, glycyl-L-tyrosine, L-Glutathione, glycylglycine, L-malic acid, and mixtures of these compounds.

17. The biocompatible, biodegradable material of claim 1, which has a hard segment content in the range of 5% to 100% and a soft segment which forms the remaining part of the material.

18. The biocompatible, biodegradable material of claim 1, which has amphiphilic properties.

19. The biocompatible, biodegradable material of claim 1, having a ratio of hydrophilic polyols to hydrophobic polyols in the range of 2:1 to 2.6:1.

20. The biocompatible, biodegradable material of claim 1, which degrades within 2 to 18 months or within 4 to 12 months.

21. The biocompatible, biodegradable material of claim 1, which has a glass transition temperature in the range of −60° C. to +70° C.

22. The biocompatible, biodegradable material of claim 1, which, upon degradation, degrades into nontoxic by-products.

23. The biocompatible, biodegradable material of claim 1, which has a molecular weight in the range of 10,000 to 300,000 dalton.

24. The biocompatible, biodegradable material of claim 1, wherein the membranous and/or spongy structure or body contains pores having a pore size in the range of 0.1 to 5,000 micrometers.

25. The biocompatible, biodegradable material of claim 1, which is designed as a scaffold suitable for bone substitute, articular cartilage repair or soft tissue repair.

26. The biocompatible, biodegradable material of claim 1, which is designed as an artificial periosteum.

27. The biocompatible, biodegradable material of claim 1, which is designed as artificial skin or as a wound dressing.

28. The biocompatible, biodegradable material of claim 1, which is designed as a cardiovascular implant, pericardial patch or a vascular prostheses.

29. The biocompatible, biodegradable material of claim 1, which is designed as a bone graft substitute.

30. The biocompatible, biodegradable material of claim 1, which is designed as an articular cartilage repair.

31. The biocompatible, biodegradable material of claim 1, which is designed as a tissue engineered scaffold.

32. The biocompatible, biodegradable material of claim 1, which contains nanosize or micrometer size calcium phosphate crystals.

33. The biocompatible, biodegradable material of claim 1, which completely degrades after a time period in the range of 1 to 24 months.

34. The biocompatible, biodegradable material of claim 1, which is designed as an internal fixation device for bone fracture treatment.

\* \* \* \* \*